United States Patent [19]

Davis

[11] Patent Number: 5,057,103

[45] Date of Patent: Oct. 15, 1991

[54] COMPRESSIVE INTRAMEDULLARY NAIL

[76] Inventor: Emsley A. Davis, P.O. Box 942, McCamey, Tex. 79752

[21] Appl. No.: 517,583

[22] Filed: May 1, 1990

[51] Int. Cl.$^5$ .............................................. A61B 17/18
[52] U.S. Cl. ........................................ 606/63; 606/68
[58] Field of Search .................................. 606/60-63, 606/66-68

[56] References Cited

U.S. PATENT DOCUMENTS

| | | | |
|---|---|---|---|
| 2,685,877 | 8/1954 | Dobelle | 606/68 X |
| 3,759,257 | 9/1973 | Fischer et al. | 606/63 |
| 3,779,239 | 12/1973 | Fischer et al. | 606/63 |
| 4,204,531 | 5/1980 | Aginsky | 606/63 |
| 4,409,974 | 10/1983 | Freedland | 606/68 X |
| 4,519,100 | 5/1985 | Wills et al. | 606/63 |
| 4,632,101 | 12/1986 | Freedland | 606/68 |
| 4,721,103 | 1/1988 | Freedland | 606/63 X |

OTHER PUBLICATIONS

Biomet, Inc., brochure, "OEC/Brooker-Wills System", Feb. 1986.
Section B, "Internal Fracture Fixation", Medical Equipment Catalog, Zimmer, Inc., 1987, pp. B54–B57, B76–B78.
Mollica et al., "Elastic Intramedullary Nailing in Shaft Fractures of the Femur & Tibia", Orthopedics, vol. 9, No. 8, Aug. 1986, pp. 1065–1077.
Crenshaw, Cambell's Operative Orthopaedics, vol. One, Fifth Ed., The C. V. Mosby Company, 1971, pp. 479–487, 553–572.
Herndon, The Surgical Clinics of North America, vol. 63, No. 3, W. B. Saunders Company, Jun. 1983, pp. 607–610, 615–622.
Perren, Russenberger, Steinemann, Müeller & Allgöwer, "A Dynamic Compression Plate", Acta Ortho. Scand. (Suppl.), vol. 125, pp. 31–41, 1969.

Primary Examiner—Robert A. Hafer
Assistant Examiner—Kerry Owens
Attorney, Agent, or Firm—Arthur F. Zobal; Geoffrey A. Mantooth

[57] ABSTRACT

A nail is inserted into the medullary canal of a fractured bone to fixate the bone segments in order to promote healing. The nail provides compressive force to close the fracture and further promote healing. The nail has an outer member and an inner member that is slidable within the outer member. The inner member has at one end arms for engaging the interior of the bone cortex in the distal bone segment and at the other end a holding member for engaging the cortex in the proximal bone segment. The arms are movable between stowed positions, for allowing the insertion of the nail into the bone, and deployed positions, for engaging the bone cortex. The force exerted by the arms and the holding member on the bone is adjustable.

22 Claims, 3 Drawing Sheets

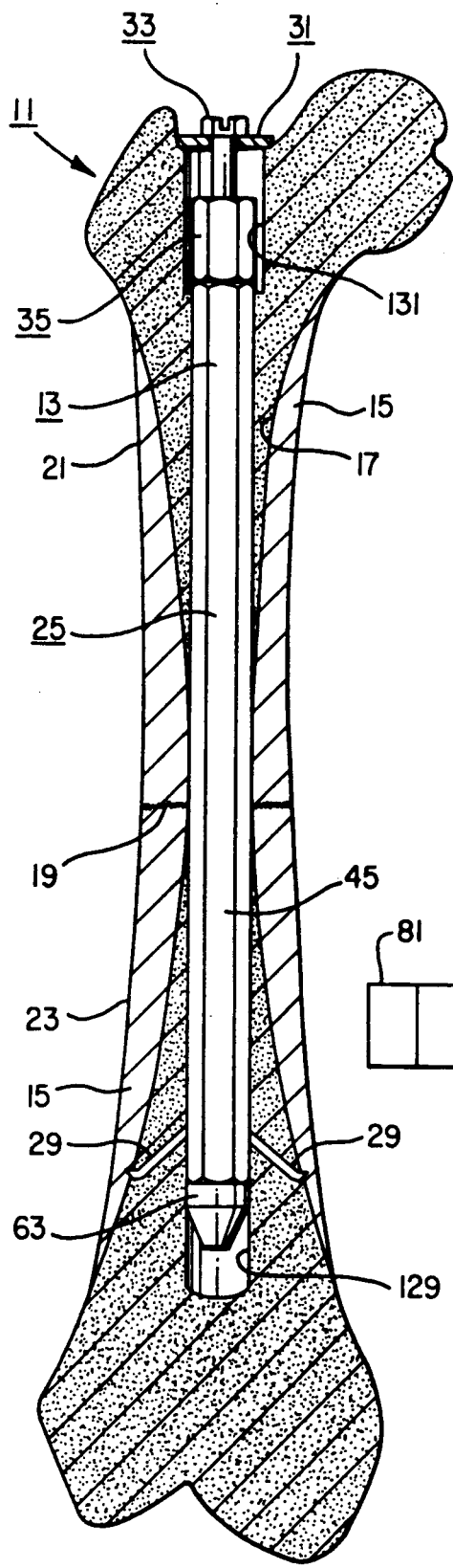
FIG. 1
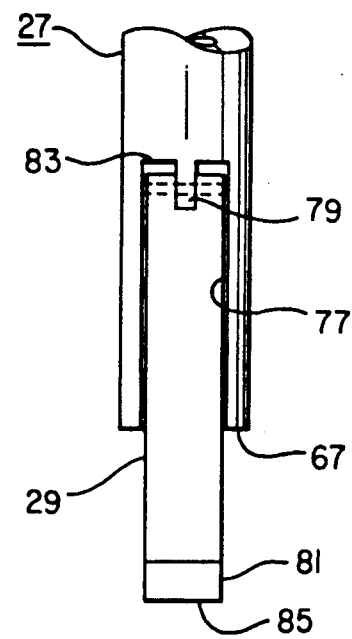
FIG. 4
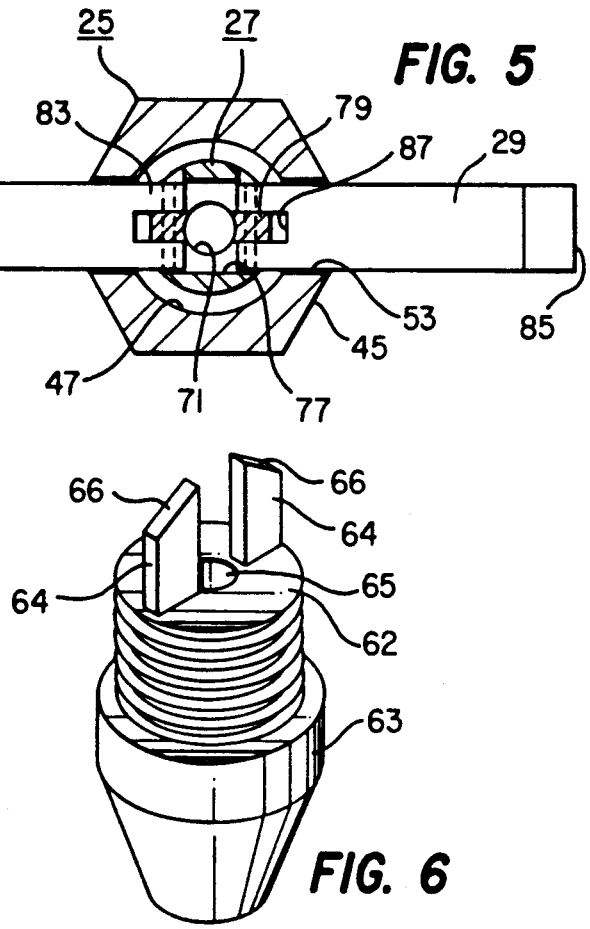
FIG. 5
FIG. 6

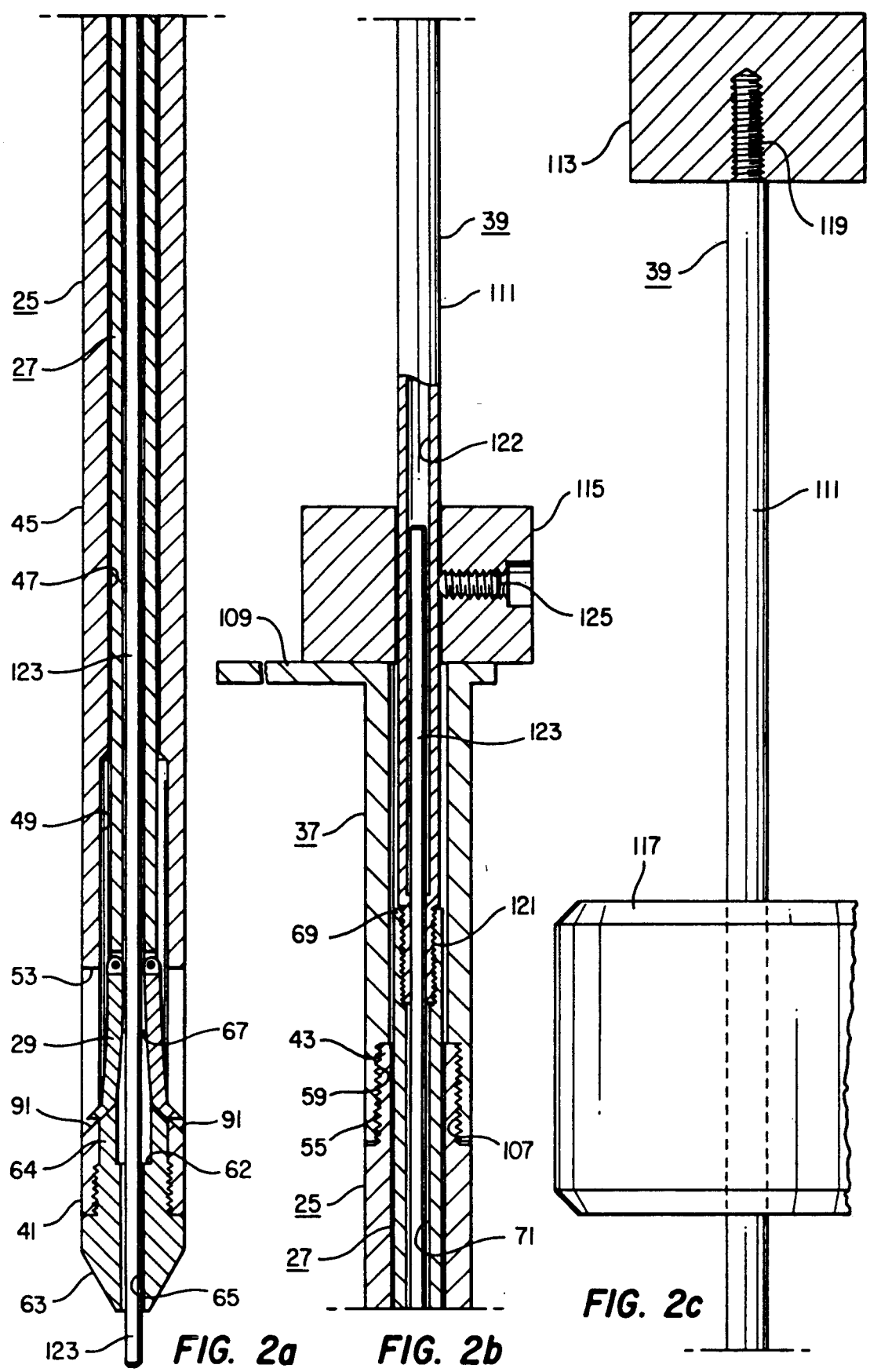

COMPRESSIVE INTRAMEDULLARY NAIL

FIELD OF THE INVENTION

The invention relates to bone nail devices that are inserted into the medullary canal of a fractured bone to promote healing of the bone fracture.

BACKGROUND OF THE INVENTION

Long bones are those greatly elongated bones such as the femur (or thigh bone) that are found in a human or in an animal. When a long bone is fractured, the surgeon immobilizes the various bone segments relative to one another to promote healing of the fracture. The immobilization or fixation of the segments is accomplished by the use of one or more rigid devices that span the fracture site and are located either external to the body or internally on the bone surface or inside the bone canal.

External fixation devices are typically located outside of the body, with the only components that enter the body and bone being metal pins. One such external device is known as a Hoffmann device. Another such device is known as a Brooker frame. Both are characterized by plural pins lodged in each bone segment. The pins are oriented transversely to the bone and exit the body. Frames that are exterior to the body connect the pins together. External devices not only prohibit movement of the bone segments relative to one another, but they also provide longitudinal compressive force on the bone segments, causing the segments to contact one another at the fracture site. Such compressive contact between the bone segments is desirable because it creates a physiological stimulus to unite the bone segments. However, external devices have many problems. External devices are difficult to manipulate to achieve the desired compressive force. Also, once the devices are set in the desired position, they can be inadvertently manipulated. Furthermore, external devices are inconvenient for the patient and present an increased chance of infection along the metal pins that penetrate the skin and underlying tissue.

Internal fixation devices include intramedullary nails which are located in the bone canal as well as cortical plates which are located on the exterior of the bone cortex. The nails or plates are implanted surgically in a single operation. Prior art nails include Schneider nails, Kuntscher nails and Ender nails. Schneider nails are longitudinally fluted rods with small teeth on the ends. The teeth allow a trough to be cut as the nail is driven down the canal. Kuntscher nails are hollow rods with longitudinal flutes. Ender nails are twin flexible rods that may be curved. Intramedullary nails reduce the risk of infection since there is no continued penetration of the skin and are inserted away from the fracture site. Intramedullary nails also prevent inadvertent manipulation. However, prior art intramedullary nails fail to provide compressive force along the length of the bone. Cortical plates, which are fastened to the bone cortex by screws, can apply compression to the bone segments. However, cortical plates are applied at the fracture site and carry the risk of infection and excessive blood loss.

SUMMARY OF THE INVENTION

It is an object of the present invention to provide an intramedullary bone nail device that, once inserted into a bone, will exert a compressive force along the length of the bone.

The nail of the present invention includes an elongated insertable member, first and second holding means and means for adjusting the force exerted by the first and second holding means. The insertable member has a longitudinal axis, first and second end portions and has an exterior surface. The insertable member has a transverse dimension which is small enough to allow the insertion of the insertable member into the medullary canal of a bone. The first holding means is located at the insertable member first end portion. The first holding means is adapted for engaging the bone cortex and for holding the first end portion in position relative to the bone cortex when so engaged. The first holding means is expandable into an engagement position from a stowed position in the insertable member, wherein the insertable member first end portion can be inserted into the medullary canal of the bone when the first holding means is in the stowed position. The second holding means is coupled with the insertable member second end portion. The second holding means is adapted for engaging the bone cortex and for holding the second end portion in position relative to the bone cortex when so engaged. The means for adjusting the force exerted by the first and second holding means on the bone along the longitudinal axis is coupled with the first and second holding means, wherein the device is adapted to be inserted into the medullary canal of the bone so as to span the site of the bone fracture with the first holding means on one side of the fracture site and the second holding means on the other side of the fracture site. The device is adapted to exert compressive force onto the bone across the fracture site with the first and second holding means.

In one aspect, outer and inner members are provided. The outer member has first and second end portions and a passage extending therethrough. The inner member is located in said passage and extends between the first and second end portions of the outer member. The outer member has openings located at the first and second end portions. The first holding means is coupled to the inner member first end. When the first holding means is in the deployed position, the first holding means protrudes out from the outer member through the outer member first end opening and when the first holding means is in the stowed position the first holding means is located in the outer member such that the outer member can be inserted into the medullary canal.

In another aspect, the first holding means includes plural arms that are pivotally coupled to the inner member. The arms have free ends that include snag means for snagging the cortex and providing that the pivotable arms securely engage the bone cortex.

In still another aspect, there is provided a retaining means that includes a cap that is coupled to the outer member second end portion. The cap has an opening that is aligned with the outer member second end portion opening. The cap opening is of a smaller diameter than the outer member second end portion opening, wherein the cap opening limits the movement of the inner member towards the outer member second end portion when said arms are in the deployed position. In still another aspect, the exterior surface of the outer member is polygonal in transverse cross-section.

The nail of the present invention is inserted remotely from the fracture site into the medullary canal of the fractured bone. Installation of the nail into the bone occurs at the end of the bone (away from the fracture site) instead of at the middle portion of the bone, thereby lessening the chance of complications and shortening the period of hospitalization of the patient. The nail fixes the bone segments together, preventing rotation, angulation and shearing. Furthermore, the nail exerts a compressive force along the longitudinal axis of the bone. This compressive force promotes healing, resulting in earlier rehabilitation of the patient.

BRIEF DESCRIPTION OF THE DRAWINGS

FIG. 1 is a schematic longitudinal cross-sectional view of human femur showing the installed compressive intramedullary nail of the present invention, in accordance with a preferred embodiment.

FIGS. 2a-2c are longitudinal cross-sectional views of the compressive nail of FIG. 1 with the compressive nail configured for insertion into the bone. As shown in FIGS. 2a-2c, the top of the nail portion shown in FIG. 2a is connected to the bottom of the nail portion shown in FIG. 2b, and the top of FIG. 2b is connected to the bottom of FIG. 2c.

As shown in FIGS. 3a and 3b, the top of the nail portion shown in FIG. 3a is connected to the bottom of the nail portion shown in FIG. 3b.

FIG. 4 is a side view of the inner member, showing a pivotable arm.

FIG. 5 is a transverse cross-sectional view of the nail, taken through lines V—V of FIG. 3a.

FIG. 6 is an isometric view of the cap member.

DESCRIPTION OF THE PREFERRED EMBODIMENT

Figure 3A:
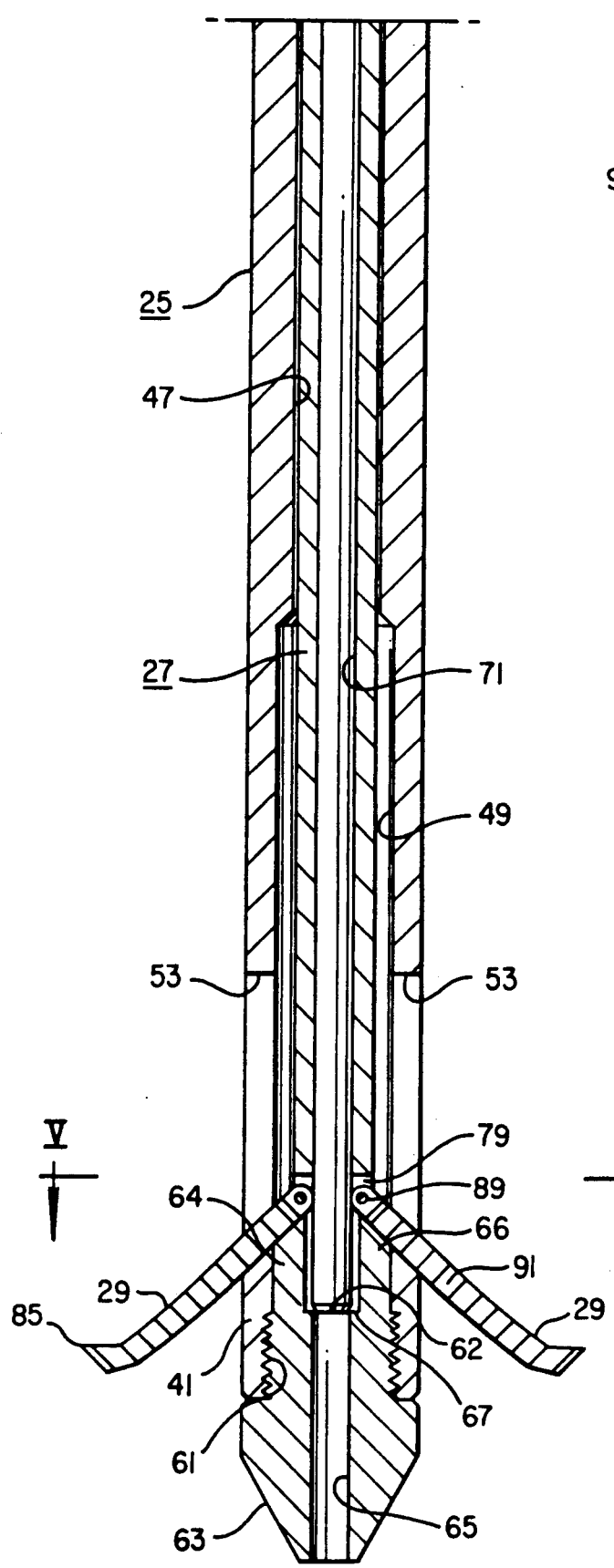
FIGS. 3a and 3b are longitudinal cross-sectional views of the compressive nail configured for exerting compressive forces on a bone.

In FIG. 1, there is shown a longitudinal cross-sectional view of a long bone 11 in which the compressive intramedullary nail 13, in accordance with a preferred embodiment, has been installed. The long bone 11 shown in FIG. 1 is a human femur or thigh bone. The bone 11 has a cortex 15, which is the hard outer layer, and a medullary or femoral canal 17 containing the soft bone marrow. The bone 11 has a fracture site 19 which divides the bone into a proximal segment 21 (nearest to the surgeon) and a distal segment 23 (furthest from the surgeon).

The nail 13 includes an outer member 25, an inner member 27, first holding means 29, second holding means 31, a force adjustment bolt 33, and a retaining cap 35. A handle 37 and an extractor/impactor 39 are provided to aid in the insertion and the removal of the nail 13 from the bone.

Referring to FIGS. 1-3b, the elongated outer member 25 has first and second ends 41, 43 and a longitudinal axis extending therebetween. The outer member 25 has an exterior surface 45 that is generally polygonal in transverse cross-section. In the preferred embodiment, the exterior surface is hexagonal in shape. The transverse diameter of the outer member 25 is small enough so as to allow the insertion of the compressive nail 13 into the medullary canal 17. The outer member 25 is tubular, with an interior cylindrical passage 47 extending longitudinally between the first and second ends 41, 43. A counterbore 49 extends from the first end 41 towards the second end 43. Openings at the first and second ends 41, 43 of the outer member 25 allow communication between the passage 47 and the exterior of the outer member. There are also plural slotted openings 53 in the outer member 25 near the first end 41.

These slotted openings 53, which are longitudinally oriented, allow communication between the passage 47, and more specifically the counterbore 49, and the exterior of the outer member. In the preferred embodiment, there are two openings 53, located 180 degrees apart on the outer member. The second end 43 of the outer member has exterior threads 55 for receiving interior threads 57 of the retaining cap 35 (see FIG. 3b) and interior threads 59 of the handle 37 (see FIG. 2b). The first end 41 of the outer member 25 has interior threads 61, in the passage 47, for receiving exterior threads on a cap member 63.

The cap member 63 caps the first end 41 of the outer member 25 and the passage 47. The cap member 63 is frusto-conical in shape such that the outer end of the cap member is smaller than the outer member. The cap member 63 tapers the outer member first end 41 to provide for ease of insertion into the medullary canal 17 and past the fracture site 19. The cap member 63 has a longitudinal passage 65 therethrough, which passage is coaxial with the outer member passage 47. The cap member 63 has a top surface 62 that is perpendicular to the longitudinal axis of the passage 65. Two diametrically opposed plates 64 extend longitudinally outward from the top surface 62, as shown in FIG. 6. The plates 64 prevent the arms 29 from jamming during deployment. The plates 64 extend from the outer edge of the top surface 62 towards the passage 65. The outer edge 66 of each plate 64 is beveled 45 degrees. When the cap member 63 is assembled onto the outer member 25, the plates 64 are aligned with the slots 53 such that the beveled edges 66 are coplanar with respective inclined surfaces 91 on the outer member 25. Each plate 64 is narrow in width so as to be received by a slot 77 at the end of the inner member 27.

The inner member 27 is a cylindrical tube with first and second ends 67, 69 and a passage 71 extending there between. The length of the inner member 27 is such that the inner member extends from the outer member second end 43 to the openings 53. The outside diameter of the inner member 27 is small enough such that the inner member can be slid longitudinally into the insertable member passage 47. The second end 69 of the inner member 27 has internal threads 73 for matingly engaging external threads 75 on the force adjustment bolt 33. Referring to FIGS. 4 and 5, the first end 67 of the inner member 27 is bifurcated by a slot 77 so as to form two end portions. Two mounting projections 79 project from the closed end of the slot toward the open end. The mounting projections 79 are integral with the wall of the inner member and are positioned 180 degrees apart.

The first holding means 29 includes plural arms that are pivotally coupled to the inner member 27. Each arm 29 has a free end 81 and a fixed end 83. The free ends 81 are bent slightly and have a sharp edge 85 for snagging the interior surface of the bone cortex 15. Each fixed end. 83 is bifurcated by a notch 87 that receives a respective mounting projection 79. The arms 29 are pivotally coupled to the respective mounting projections 79 by a respective pin 89 that extends through the fixed end 83 of the respective arm 29 and the mounting projection 79. Thus, the mounting projections 79, the fixed ends 83 and the pins 89 form a hinge. The respective pins 89 are securely coupled to the respective arms 29. For example, the pins may be welded to the arms.

Figure 3B:
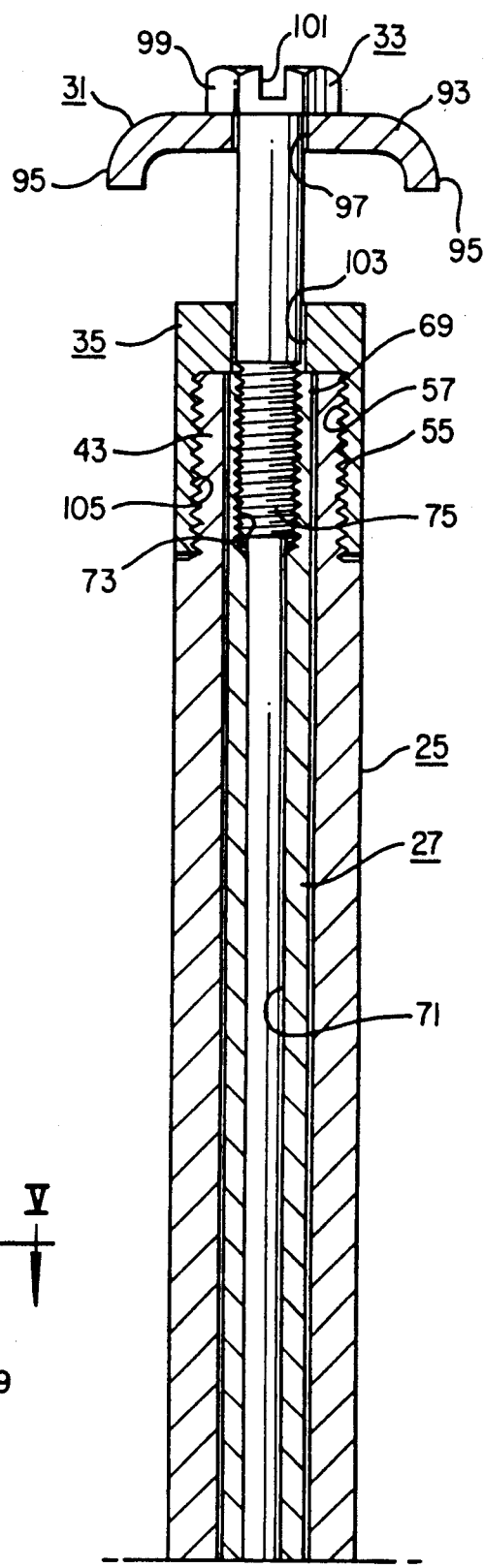

The arms 29 pivot between stowed positions as shown in FIG. 2a, wherein the arms are located within the outer member 25, and deployed positions as shown in FIG. 3a, wherein the arms extend outwardly from the outer member through the slotted openings 53. The arms 29 can be remotely manipulated between the stowed and deployed positions from the top end 43 of the outer member by sliding the inner member 27 relative to the outer member. When the inner member 27 is slid away from the outer member first end 41, as shown in FIGS. 2a and 2b, the arms 29 are in the stowed position. When the inner member 27 is slid toward the outer member first end 41, as shown in FIGS. 3a and 3b, the arms are extended to the deployed position. The openings 53 are provided with inclined surfaces 91 at the ends of the openings that are closest to the outer member first end 41. In the preferred embodiment, the inclined surfaces 91 are inclined 45 degrees from the longitudinal axis. Coplanar with the inclined surfaces 91 are the beveled edges 66 of the cap member plates 64. As the inner member 27 is slid toward the first end 41 of the outer member 25, the arms 29 contact the inclined surfaces 91 and the edges 66 and are forced outwardly. The edges 66 prevent jamming of the arms 29 during deployment. The slotted first end 67 of the inner member travels past the edges 66 to abut the top surface 62 of the cap member 63. When the arms 29 are in the deployed position, the first end 41 of the inner member contacts the cap member 63, thereby preventing any further movement of the inner member 27 relative to the outer member 25, and the inclined surfaces 91 contact flat portions of the arms 29 to provide support.

The second holding means 31 is an inverted shallow U-shaped member. The member 31 has a main wall 93 with integral side walls 95 extending perpendicularly therefrom. The main wall 93 has a circular opening 97 for receiving the force adjustment bolt 33. The bolt 33 can slide in and out of the opening 97. The member 31 is oriented on the shaft of the force adjustment bolt 33 such that the side walls 95 extend toward the outer member first end 41, as shown in FIGS. 3a and 3b. The bolt 33 is screwed into the second end 69 of the inner member 27. The bolt 33 has a hexagonal head 99 for receiving a socket wrench and a slot 101 for receiving a slotted surgical screw driver.

Referring to FIG. 3b, the retaining cap 35 is generally hexagonal with a central longitudinal bore 103 therethrough. The bore 103 receives the shaft of the force adjustment bolt 33. A counterbore 105 is formed in one end. The counterbore 105 has internal threads for coupling to the threads 55 on the outer member second end 43.

Referring to FIG. 2b, the handle 37 is generally cylindrical and tubular with one end having integral threads 107 for matingly engaging the external threads 55 on the second end 43 of the outer member 25 and with the other end of the handle having an integral flange 109 that extends radially outward in one direction. The inside diameter of the handle 37 receives the inner member and the extractor/impactor 39.

The extractor/impactor 39 includes a rod 111, first and second stops 113, 115, and a throw weight 117. The rod 111 is threaded on both ends. The first end 119 is threaded into the first stop 113 while the second end 121 is adapted to be threaded into the inner member second end 69. The second end 121 of the rod 111 has a bore 122 therein to receive a guide wire 123 during insertion of the nail 13 into the bone 11. The second stop 115 and the throw weight 117 are free to move along the rod 111. The second stop 115 has a set screw 125 for locking the second stop to the rod 111 and preventing sliding movement. The throw weight 117 is located between the first and second stops 113, 115.

The use of the compressive intramedullary nail 13 in the bone 11 will now be described. (In FIGS. 2a-3b, the bone surrounding the compressive nail 13 is not shown for clarity.) The patient is prepared for surgery and positioned advantageously so that imaging equipment (such as a fluoroscope) can be used on the bone 11. Manual reduction to align th bone segments is performed under fluoroscopy. The patient is then entered in the hip region to gain access to the upper end of the proximal segment 21 of the bone 11. The point of entry is away from the fracture site, thereby reducing the risk of complications due to infection and blood loss. A hole is drilled through the cortex 15 in the upper end of the proximal segment 21 so that the medullary canal 17 can be entered. With the aid of the imaging equipment, the guide wire 123 is passed down the medullary canal 17 of the proximal segment 21 across the fracture site 19 and into the medullary canal of the distal segment 23. Reamers (not shown) are then used to remove bone marrow from the medullary canal 17 to form a drilled hole 127. The reamers use the guide wire 123 for guidance down the canal 17 and across the fracture site 10. Successively larger diameter reamers are used to remove the bone marrow and to gauge the diameter of the canal 17 at its narrowest point. This information is used to select an appropriate size nail 13, wherein a nail is chosen that forms an interference fit with the narrowest portion of the canal 17. A larger diameter counterbore 131 is drilled into the proximal end of the proximal segment 21. The counterbore 131 receives the retaining cap 35. The drilled hole 105 is then cleared of everything except the guide wire 123 which is left intact.

Next, the nail 13 is readied for insertion into the medullary canal 17, as shown in FIGS. 2a-2c. The inner member 27 is inserted into the outer member 25 such that the arms 29 are in the stowed position. Insertion of the inner member 27 is through the first end 41 of the outer member 25 such that the counterbore 49 receives the arms 29. The cap member 63 is removed from the outer member to allow insertion of the inner member. After insertion, the cap member 63 is replaced. The handle 37 is threaded onto the second end 43 of the outer member. The second end 121 of the extractor/impactor rod 111 is threaded into the second end 69 of the inner member and the second stop 115 is slid along the rod 111 until it contacts the handle flange 109 as shown in FIG. 2b. Then, the set screw 125 is tightened. By setting the second stop 115 against the handle flange 109, the inner member 27 is prevented from moving toward the outer member first end 41, thereby preventing the arms 29 from deploying during the insertion procedure.

The nail 13 is then inserted into the canal 17 along the guide wire 123. The guide wire 123 enters the nail 13 through the cap member passage 65 and the inner member passage 71. The compressive nail 13 is driven through the narrowest portion of the canal 17 by repeatedly throwing the weight 117 along the rod 111, striking the second stop 115. As the distal end of the nail 13 is driven through the fracture site 19, the cap member 63, with its tapered end, aligns the proximal and distal bone segments 21, 23 so that the medullary canals of the segments are aligned with each other. The progress of the nail 13 in the canal 17 is monitored by using the imaging equipment.

When the nail 13 is in the desired position inside of the bone 11, the arms 29 can be deployed. The set screw 125 of the second stop 115 is loosened and the second stop is moved a short distance along the rod toward the first stop 113, where the set screw 125 is retightened. Force is exerted on the extractor/impactor 39 to move the inner member 27 toward the outer member first end 41 in order to deploy the arms 29 to their full extent. Such force can be achieved by repeatedly throwing the weight 117 against the second stop 115. As the arms 29 expand outwardly, they force their way through the soft bone marrow tissue. When the arms 29 are fully deployed, as shown in FIGS. 3a–3b, the first end 67 of the inner member 27 abuts against the cap member 63 and the arms, which are at a 45 degree angle, contact the inclined surfaces 91 and the edges 66. The extractor/impactor 39 and the handle 27 are removed from the nail.

The length of the outer member 25 is such that when the arms 29 engage the cortex 15, the second end 43 of the outer member is located within the medullary canal 17. The retaining cap 35 is inserted into the counterbore 131 of the canal 17 and is screwed onto the second end 43 of the outer member 25. The diameter of the bore 103 of the retaining cap 35 is smaller than the outside diameter of the inner member 27. Thus, the retaining cap 35 retains the inner member 27 in its innermost position and thus keeps the arms 29 in the deployed position. A socket wrench can be used to assemble the retaining cap 35 onto the outer member 25. The hexagonal shape of the exterior surface 45 of the outer member 25 prevents rotation of the compressive nail within the canal 17.

Next, the force adjustment bolt 33, with the second holding means member 31 thereon, is inserted through the opening 103 of the retaining cap 35 and is screwed into the second end 69 of the inner member 27. As shown in FIG. 1, the second holding means member 31 is located outside of the bone cortex 15, while the remainder of the nail is located inside of the bone cortex. The bolt 33 is rotated with a socket wrench or a screwdriver until the bolt head 91 causes the member 31 to firmly engage the outer surface of the bone cortex 15. Then, using the imaging equipment, the bolt 33 is rotated to shorten the distance between the arms 29 and the member 31, thereby bringing the proximal and distal segments 21, 23 closer together. This tightening of the bolt is continued until the fracture line 19 is appreciably eliminated as shown by the imaging equipment. As the bolt 33 is tightened, the snags 85 in the arms 29 engage the interior of the bone cortex. The arms 29, the inner member 27, and the member 31 exert compressive force along the longitudinal axis of the bone forcing the two bone segments 21, 23 together at the fracture site 19. The amount of compressive force exerted on the bone is adjusted by either tightening or loosening the bolt 33. The amount of compressive force applied to the bone can vary between 0 pounds-force (where the segments are merely brought into contact with each other) to some maximum value, which if exceeded would cause necrosis of the bone tissue. The maximum compressive force that can be safely applied to a bone depends on the type of bone being fixed (e.g. femur, tibia), the age of the patient, and whether the patient is a human or an animal. One study has shown that in tibia fixation for sheep ranging in age between 2–4 years, forces of 70–180 kiloponds (about 150–330 pounds-force) were safely applied. Perren, Russenberger, Steinemann, Muller and Allgower, "A Dynamic Compression Plate", Acta Orthop. Scand. (Suppl.), Vol. 125, pp. 31–41, 1969. A surgeon, when installing the nail, will typically use a torque wrench to monitor the torque applied to the bolt 33. This gives the surgeon information on the compressive force being exerted by the nail on the bone. Typical torque values are 60–80 foot-pounds as applied to the bolt 33. The arms 29 are reinforced by the inclined surfaces 91 and the edges 66. After the bone is set and the desired compressive force is achieved, the patient is closed, leaving the nail 13 intact inside of the bone 11.

The nail remains inside of the patient until the fracture is healed. During this time, the patient can lead a life unhampered by the nail, because the nail is located inside of the bone. The nail, and in particular the outer member 25, fixates the bone segments, preventing angulation, rotation and shearing of the bone segments. The inner member 27, the arms 29 and the member 31 provide the necessary compressive force. The nail obviates the need for external fixation of the bone. Healing is speeded up because the compressive contact between the bore segments creates a physiological stimulus that promotes healing.

Removal of the nail 13 from the bone 11 is performed by reversing the installation steps described hereinabove. The bolt 33, the member 31 and the retaining cap 35 are all removed from the patient. After the nail 13 has been left inside of the bone for any extended period of time, bone marrow tissue will grow into the void areas around the nail. With the extractor/impactor 39, the nail can be freed of the marrow. The rod 111 of the extractor/impactor is threaded into the second end 69 of the inner member 27. The throw weight 117 is then repeatedly thrown toward the first stop 113 to loosen the inner member 27 and in particular the arms 29. The inner member 27 is moved upwardly so as to stow the arms 29. Once the arms 29 are stowed, the nail may be removed from the canal 17. The patient is then closed. The bone marrow will regenerate and fill in the void left by the nail 13.

The bone nail is made of stainless steel, a material that is capable of withstanding the necessary tensile stresses and that is acceptable to a human's biological system without being rejected. In the preferred embodiment, the pins 89 each have a shear strength of 65 pounds and the mounting projections have a 69 pound shear strength. The arms 29 are 0.174 inches wide and 0.078 inches thick. The inner member 27 has an outside diameter of 0.263 inches and an inside diameter of 0.136 inches. The outer member 25 has an outside diameter of 0.512 inches and an inside diameter of 0.281 inches. The diameter of the counterbore 49 is 0.341 inches. The length of the outer member 25 is 0.787 inches. The length of the member 31 between the side walls 95 is 0.886 inches and is 0.788 inches wide. The dimensions may vary, depending on which bone which is to be fixated. Thus, nails embodying the invention will have assorted lengths and diameters. A nail in a femur will be larger than one in a tibia, for example.

Although the nail has been described as being used in a human femur, the nail can be used in other human bones, adult and child, and can also be used in animal bones.

The inner member 27 may be completely removed from the outer member 25. Thus, another inner member, for example on with a different arm configuration, can be substituted for the original inner member 27.

The foregoing disclosure and the showings made in the drawings are merely illustrative of the principles of the present invention and are not to be interpreted in a limiting sense.

I claim:

1. A device for use in promoting healing of a fractured bone in a human or animal, said bone having a cortex, a medullary canal and a fracture site, comprising:
   a) an elongated insertable member having a longitudinal axis, a first end portion, and a second end portion, and having an exterior surface, said insertable member having a transverse dimension which is small enough to allow the insertion of said insertable member into the medullary canal of said bone;
   b) first holding means located at said insertable member first end portion, said first holding means being adapted for engaging said bone cortex and for holding said first end portion in position relative to said bone cortex when so engaged;
   c) said first holding means being expandable into an engagement position from a stowed position in said insertable member, wherein said insertable member first end portion can be inserted into the medullary canal of said bone when said first holding means is in said stowed position;
   d) second holding means coupled with said insertable member second end portion, said second holding means being adapted for engaging said bone cortex and for holding said second end portion in position relative to said bone cortex when so engaged;
   e) means for adjusting the force exerted by said first and second holding means on said bone along said longitudinal axis, said force adjustment means being coupled with said first and second holding means, wherein said device is adapted to be inserted into the medullary canal of said bone so as to span the site of said bone fracture with said first holding means on one side of said fracture site and said second holding means on the other side of said fracture site, said device being adapted to exert compressive force onto said bone across said fracture site with said fist and second holding means;
   f) said first holding means comprising plural arms that are pivotable between said stowed position and said engagement position;
   g) said second holding means comprising a flanged cap member that is adapted to engage an outer surface of said bone cortex;
   h) said pivotable arms of aid first holding means have free ends that are adapted for engaging said bone cortex, said pivotable arms comprising snag means for snagging said cortex and for providing that said pivotable arms securely engage said bone cortex, said snag means being located at the free ends of said pivotable arms.

2. The device of claim 1 wherein each of said snag means comprises a projection extending from said free end of each pivotable arm, each of said projections having a sharp edge that is adapted to engage an interior surface of said bone cortex.

3. A device for insertion into a bone, said bone having a medullary canal, a cortex and a fracture site, comprising:
   (a) an outer member having a longitudinal axis extending between first and second end portions, said outer member having an exterior surface and a transverse dimension which is small enough to allow the insertion of said outer member into the medullary canal of said bone, said outer member having a passage therein which passage extends between said first and second end portions, said passage having openings to communicate with said exterior surface, said openings being located at said first and second end portions;
   (b) an inner member located in said passage, said inner member extending between said first and second end portions of said outer member, said inner member having first and second ends that are oriented so as to be adjacent to said first and second end portions of said outer member respectively, said inner member being movable longitudinally within said passage;
   (c) first holding means coupled to said inner member first end, said first holding means being adapted to engage said bone cortex, said first holding means being expandable into a deployed position from a stowed position, wherein said first holding means protrudes out from said outer member and through said outer member first end opening when said first holding means is in the deployed position and wherein when said first holding means is in the stowed position said first holding means is located in said outer member such that said outer member can be inserted into said medullary canal, said inner member moving longitudinally in said outer member to manipulate said first holding means between said deployed and stowed positions;
   (d) second holding means coupled to said inner member second end, said second holding means being adapted to engage said bone cortex;
   (e) retaining means for retaining said inner member in a position whereby said first holding means is in said deployed position, said retaining means being coupled to said inner and outer ember;
   (f) means for adjusting the force exerted by said first and second holding means on said bone along said longitudinal axis, said force adjustment means being coupled with aid first and second holding means, wherein said device is adapted to be inserted into the medullary canal of said bone so as to span the site of said bone fracture with said first holding means on one side of said fracture site and said second holding means on the other side of said fracture site, said device being adapted to exert compressive force onto said bone across said fracture site with said first and second holding means;
   (g) said first holding means comprises plural arms that are pivotally coupled to said inner member;
   (h) deploying surfaces on said outer ember at said first end portion openings, said deploying surfaces being adapted to outwardly deploy said arms when said inner member is moved toward said outer member first end portion;
   (i) said second holding means comprises a flanged cap member that is adapted to engage an outer surface of said bone cortex;
   (i) said pivotable arms of said first holding means have free end that are adapted for engaging said bone cortex, said pivotable arms comprising snag means for snagging said cortex and for providing that said pivotable arms securely engage said bone cortex, said snag means being located at the free ends of said pivotable arms.

4. A device for insertion into a bone, said bone having a medullary canal, a cortex and a fracture site, comprising:

(a) an outer member having a longitudinal axis extending between first and second end portions, said outer member having an exterior surface and a transverse dimension which is small enough to allow the insertion of said outer member into the medullary canal of said bone, said outer member having a passage therein which passage extends between said first and second end portions, said passage having openings to communicate with aid exterior surface, said openings being located at said first and second end portions;

(b) an inner member located in said passage, said inner member extending between said first and second end portions of said outer member, said inner member having first and second ends that are oriented so as to be adjacent to said first and second end portions of said outer member respectively, said inner member being movable longitudinally within said passage;

(c) first holding means coupled to said inner member first end, said first holding means being adapted to engage said bone cortex, said first holding means being expandable into a deployed position from a stowed position, wherein said first holding means protrudes out from said outer member and through said outer member first end opening when said first holding means is in the deployed position and wherein when said first holding means is in the stowed position said first holding means is located in said outer member such that said outer member can be inserted into said medullary canal, said inner member moving longitudinally in said outer member to manipulate said first holding means between said deployed and stowed positions;

(d) second holding means coupled to said inner member second end, said second holding means being adapted to engage said bone cortex;

(e) retaining means for retaining said inner member in a position whereby said first holding means is in said deployed position, said retaining means being coupled to said inner and outer member;

(f) means for adjusting the force exerted by said first and second holding means on said bone along said longitudinal axis, said force adjustment means being coupled with said first and second holding means, wherein said device is adapted to be inserted into the medullary canal of said bone so as to span the site of said bone fracture with said first holding means on one side of said fracture site and said second holding means on the other side of said fracture site, said device being adapted to exert compressive site with said first and second holding means;

(g) said first holding means comprises plural arms that are pivotally coupled to said inner member;

(h) deploying surfaces on said outer member at said first end portion openings, said deploying surfaces being adapted to outwardly deploy said arms when said inner member is moved toward said outer member first end portion;

(i) said second holding means comprises a flanged cap member that is adapted to engage an outer surface of said bone cortex;

(j) said retaining means comprises a retaining cap that is coupled to aid outer member second end portion, said retaining cap having an opening that is aligned with said outer member second end portion opening, said retaining cap opening being of a smaller diameter than said inner member second end, wherein said cap opening limits the movement of said inner member towards said outer member second end portion when said arms are in said deployed position.

5. A device for insertion into a bone, said bone having a medullary canal, a cortex and a fracture site, comprising:

(a) an outer member having a longitudinal axis extending between first and second end portions, said outer member having an exterior surface and a transverse dimension which is small enough to allow the insertion of said outer member into the medullary canal of said bone, said outer member having a passage therein which passage extends between said first and second end portions, said passage having openings to communicate with said exterior surface, said openings being located at said first and second end portions;

(b) an inner member located in said passage, said inner member extending between said first and second end portions of said outer member, said inner member having first and second ends that are oriented so as to be adjacent to said first and second end portions of said outer member respectively, said inner member being movable longitudinally within said passage;

(c) first holding means coupled to said inner member first end, said first holding means being adapted to engage said bone cortex, said first holding means being expandable into a deployed position from a stowed position, wherein said first holding means protrudes out from said outer member and through said outer member first end opening when said first holding means is in the deployed position and wherein when said first holding means is in the stowed position said first holding means is located in said outer member such that said outer member can be inserted into said medullary canal, said inner member moving longitudinally in said outer member to manipulate said first holding means between said deployed and stowed positions;

(d) second holding means coupled to said inner member second end, said second holding means being adapted to engage said bone cortex;

(e) retaining means for retaining said inner member in a position whereby said first holding means is in said deployed position, said retaining means being coupled to said inner and outer member;

(f) means for adjusting the force exerted by said first and second holding means on said bone along said longitudinal axis, said force adjustment means being coupled with said first and second holding means, wherein said device is adapted to be inserted into the medullary canal of said bone so as to span the site of said bone fracture with said first holding means on one side of said fracture site and said second holding means on the other side of said fracture site, said device being adapted to exert compressive force onto said bone across said fracture site with said first and second holding means;

(g) said first holding means comprises plural arms that are pivotally coupled to said inner member;

(h) said inner member has a passage therein extending between said inner member first and second ends, said passage being adapted for receiving a guide wire for use in inserting said device into said medullary canal.

6. A device for insertion into a bone, said bone having a medullary canal, a cortex and a fracture site, comprising:

(a) an outer member having a longitudinal axis extending between first and second end portions, said outer member having an exterior surface and a transverse dimension which is small enough to allow the insertion of said outer member into the medullary canal of said bone, said outer member having a passage therein which passage extends between said first and second end portions, said passage having openings to communicate with said exterior surface, said openings being located at said first and second end portions;

(b) an inner member located in said passage, said inner member extending between said first and second end portions of said outer member, said inner member having first and second ends that are oriented so as to be adjacent to said first and second end portions of said outer member respectively, said inner member being movable longitudinally within said passage;

(c) first holding means coupled to said inner member first end, said first holding means being adapted to engage said bone cortex, said first holding means being expandable into a deployed position from a stowed position, wherein said first holding means protrudes out from said outer member and through said outer member first end opening when said first holding means is in the deployed position and wherein when said first holding means is in the stowed position said first holding means is located in said outer member such that said outer member can be inserted into said medullary canal, said inner member moving longitudinally in said outer member to manipulate said first holding means between said deployed and stowed positions;

(d) second holding means coupled to said inner member second end, said second holding means being adapted to engage said bone cortex;

(e) retaining means for retaining said inner member in a position whereby said first holding means is in said deployed position, said retaining means being coupled to said inner and outer member;

(f) means for adjusting the force exerted by said first and second holding means on said bone along said longitudinal axis, said force adjustment means being coupled with said first and second holding means, wherein said device is adapted to be inserted into the medullary canal of said bone so as to span the site of said bone fracture with said first holding means on one side of said fracture site and said second holding means in the other side of said fracture site, said device being adapted to exert compressive force onto said bone across said fracture site with said first and second holding means;

(g) said first holding means comprises plural arms that are pivotally coupled to said inner member;

(h) said pivotable arms of said first holding means have free ends that are adapted for engaging said bone cortex, said pivotable arms comprising snag means for snagging said cortex and for providing that said pivotable arms securely engage said bone cortex, said snag means being located at the free ends of said pivotable arms.

7. A device for insertion into a bone, said bone having a medullary canal, a cortex and a fracture site, comprising:

(a) an outer member having a longitudinal axis extending between first and second end portions, said outer member having an exterior surface and a transverse dimension which is small enough to allow the insertion of said outer member into the medullary canal of said bone, said outer member having a passage therein which passage extends between said first and second end portions, said passage having openings to communicate with said exterior surface, said openings being located at said first and second end portions;

(b) an inner member located in said passage, said inner member extending between said first and second end portions of said outer member, said inner member having first and second ends that are oriented so as to be adjacent to said first and second end portions of said outer member respectively, said inner member being movable longitudinally within said passage;

(c) first holding means coupled to said inner member first end, said first holding means being adapted to engage said bone cortex, said first holding means being expandable into a deployed position from a stowed position, wherein said first holding means protrudes out from said outer member and through said outer member first end opening when said first holding means is in the deployed position and wherein when said first holding means is in the stowed position said first holding means is located in said outer member such that said outer member can be inserted into said medullary canal, said inner member moving longitudinally in said outer member to manipulate said first holding means between said deployed and stowed positions;

(d) second holding means coupled to said inner member second end, said second holding means being adapted to engage said bone cortex;

(e) retaining means for retaining said inner member in a position whereby said first holding means is in said deployed position, said retaining means being coupled to said inner and outer member;

(f) means for adjusting the force exerted by said first and second holding means on said bone along said longitudinal axis, said force adjustment means being coupled with said first and second holding means, wherein said device is adapted to be inserted into the medullary canal of said bone so as to span the site of said bone fracture with said first holding means on one side of said fracture site and said second holding means on the other side of said fracture site, said device being adapted to exert compressive force onto said bone across said fracture site with said first and second holding means;

(g) said first holding means comprises plural arms that are pivotally coupled to said inner member;

(h) said retaining means comprises a retaining cap that is coupled to said outer member second end portion, said retaining cap having an opening that is aligned with said outer member second end portion opening, said retaining cap opening being of a smaller diameter than said inner member second end, wherein said cap opening limits the movement of said inner member towards said outer member second end portion when said arms are in said deployed position.

8. A device for insertion into a bone, said bone having a medullary canal, a cortex and a fracture site, comprising:
   (a) an outer member having a longitudinal axis extending between first and second end portions, said outer member having an exterior surface and a transverse dimension which is small enough to allow the insertion of said outer member into the medullary canal of said bone, said outer member having a passage therein which passage extends between said first and second end portions, said passage having openings to communicate with said exterior surface, said openings being located at said first and second end portions;
   (b) an inner member located in said passage, said inner member extending between said first and second end portions of said outer member, said inner member having first and second ends that are oriented so as to be adjacent to said first and second end portions of said outer member respectively, said inner member being movable longitudinally within said passage;
   (c) first holding means coupled to said inner member first end, said first holding means being adapted to engage said bone cortex, said first holding means being expandable into a deployed position from a stowed position, wherein said first holding means protrudes out from said outer member and through said outer member first end opening when said first holding means is in the deployed position and wherein when said first holding means is in the stowed position said first holding means is located in said outer member such that said outer member can be inserted into said medullary canal, said inner member moving longitudinally in said outer member to manipulate said first holding means between said deployed and stowed positions;
   (d) second holding means coupled to said inner member second end, said second holding means being adapted to engage said bone cortex;
   (e) retaining means for retaining said inner member in a position whereby said first holding means is in said deployed position, said retaining means being coupled to said inner and outer member;
   (f) means for adjusting the force exerted by said first and second holding means on said bone along said longitudinal axis, said force adjustment means being coupled with said first and second holding means, wherein said device is adapted to be inserted into the medullary canal of said bone so as to span the site of said bone fracture with said first holding means on one side of said fracture site and said second holding means on the other side of said fracture site, said device being adapted to exert compressive force onto said bone across said fracture site with said first and second holding means;
   (g) said first holding means comprises plural arms that are pivotally coupled to said inner member;
   (h) said exterior surface of said outer member is polygonal in transverse cross-section.

9. A device for insertion into a bone, said bone having a medullary canal, a cortex and a fracture site, comprising:
   (a) an outer member having a longitudinal axis extending between first and second end portions, said outer member having an exterior surface and a transverse dimension which is small enough to allow the insertion of said outer member into the medullary canal of said bone, said outer member having a passage therein which passage extends between said first and second end portions, said passage having openings to communicate with said exterior surface, said openings being located at said first and second end portions;
   (b) an inner member located in said passage, said inner member extending between said first and second end portions of said outer member, said inner member having first and second ends that are oriented so as to be adjacent to said first and second end portions of said outer member respectively, said inner member being movable longitudinally within said passage;
   (c) first holding means coupled to said inner member first end, said first holding means being adapted to engage said bone cortex, said first holding means being expandable into a deployed position from a stowed position, wherein said first holding means protrudes out from said outer member and through said outer member first end opening when said first holding means is in the deployed position and wherein when said first holding means is in the stowed position said first holding means is located in said outer member such that said outer member can be inserted into said medullary canal, said inner member moving longitudinally in said outer member to manipulate said first holding means between said deployed and stowed positions;
   (d) second holding means coupled to said inner member second end, said second holding means being adapted to engage said bone cortex;
   (e) retaining means for retaining said inner member in a position whereby said first holding means is in said deployed position, said retaining means being coupled to said inner and outer member;
   (f) means for adjusting the force exerted by said first and second holding means on said bone along said longitudinal axis, said force adjustment means being coupled with said first and second holding means, wherein said device is adapted to be inserted into the medullary canal of said bone so as to span the site of said bone fracture with said first holding means on one side of said fracture site and said second holding means on the other side of said fracture site, said device being adapted to exert compressive force onto said bone across said fracture site with said first and second holding means;
   (g) said first holding means comprises plural arms that are pivotally coupled to said inner member;
   (h) insertion mean for inserting and removing said outer and inner members from said bone, said insertion means comprising a rod having a fixed end and a free end, said fixed end being adapted to be removably coupled to said inner member second end, said rod having stop members thereon, said rod having throw weight means thereon, said throw weight means being movable along said rod between said stop members.

10. A device for insertion into a bone, said bone having a medullary canal, a cortex and a fracture site, comprising:
   (a) an elongated outer member having first and second end portions and a longitudinal axis extending therebetween, said outer member having a passage therein which passage extends between said first and second end portions, said passage having openings communicating with the exterior of said outer member, said openings being located at said first and second end portions, said outer member having an exterior surface that is polygonal in transverse cross-section;

(b) an elongated inner member having first and second ends, said inner member being located within said outer member passage such that said inner member first and second end are adjacent to said outer member first and second end portions respectively;

(c) first arm means adapted to engage said bone cortex, said first arm means comprising plural first arms that are pivotally coupled to said inner member first end with hinge means, said first arms being pivotable between stowed and deployed positions, wherein when said first arms are in said stowed position said first arms are located within said outer member such that said outer member can be inserted into said medullary canal and when said first arms are in said deployed position said first arms extend out from said outer member through said outer member first end portion openings, said first arms being moved between said stowed and deployed positions by sliding said inner member in said outer member, said first arms having snag means to engage said bone cortex;

(d) said outer member first end portion openings having inclined surfaces wherein when said inner member is slid in said outer member to deploy said first arms said inclined surfaces force said first arms outward;

(e) bolt means coupled to said inner member second end, said bolt means extending through said outer member second end portion opening;

(f) second arm means adapted to engage said bone cortex, said second arm means slidingly coupled to said bolt means, said second arm means comprising projections that extend radially outward from aid bolt means, wherein said bolt means can adjust the distance between said first and second arm means;

(g) a retaining cap adapted to be removably coupled to said outer member, said retaining cap having an opening for receiving said bolt means, said retaining cap having stop surfaces for preventing movement of said inner member away from said outer member first end portion when said first arms are in said deployed position in order to retain said first arms in said deployed position.

11. The device of claim 10 wherein aid inner member has a passage therein extending between said inner member first and second ends, said passage being adapted for receiving a guide wire for use in inserting said device into said medullary canal.

12. The device of claim 10 further comprising insertion means for inserting and removing said outer and inner members from said bone, said insertion means comprising a rod having a fixed end and a free end, said fixed end being adapted to be removably coupled to said inner member second end, said rod having stop members thereon, said rod having trow weight means thereon, said throw weight means being movable along said rod between said stop members.

13. The device of claim 10, further comprising:

(a) insertion means for inserting and removing said outer and inner members from said bone, said insertion means comprising a rod having a fixed end and a free end, said fixed end being adapted to be removably coupled to said inner member second end, said rod having stop members thereon, said rod having throw weight means thereon, said throw weight means being movable along said rod between said stop members;

(b) said inner member has a passage therein extending between said inner member first and second ends, said passage being adapted for receiving a guide wire for use in inserting said device into said medullary canal.

14. A method for promoting healing of a fractured long bone in a human or animal, said bone having a cortex, a medullary canal and a fracture site, said fracture site separating said bone into a proximal segment and a distal segment, comprising the steps of:

(a) entering said medullary canal from the end of said proximal segment;

(b) removing tissue from said medullary canal so as to form a passage, said passage spanning said fracture site from said proximal segment to said distal segment;

(c) providing nail means which is adapted to be inserted into said medullary canal, said nail means having first and second holding means adapted to engage said cortex, said first holding means being deployable from a stowed position, providing insertion means for inserting and removing said nail means from said bone, said insertion means having a throw weight that is movable between two stop members, said insertion means being removably coupled to said nail means;

(d) inserting said nail means into said medullary canal from said proximal segment, then inserting said nail means through said fracture site and into said distal segment such that said nail means extends from said proximal segment to said distal segment, said insertion of said nail means into said medullary canal being assisted by said insertion means, wherein said throw weight is thrown against one of said stop members so as to drive said nail means into said bone;

(e) deploying said first holding means so that said first holding means engages an interior surface of the cortex of said distal segment;

(f) coupling said second holding means onto said nail means in said proximal segment;

(g) engaging said second holding means with the cortex of said proximal segment;

(h) adjusting the distance between said first and second holding means to close the fracture site and to bring the proximal and distal segments into compressive contact with each other across the fracture site;

(i) exiting said medullary canal while leaving said nail means in place.

15. The method of claim 14 further comprising the step of inserting guide wire means into said medullary canal from said proximal segment through said fracture site and into said distal segment, then inserting said nail means into said medullary canal along said guide wire means and then removing said guide wire means after said nail means has been inserted into said bone.

16. The method of claim 15 wherein said second holding means engages an outside surface of the cortex of said proximal segment.

17. The method of claim 16 wherein said nail means is chosen so as to have a transverse diameter that will produce an interference fit with the narrowest portion of said medullary canal.

18. The method of claim 14 wherein said second holding means engages an outside surface of the cortex of said proximal segment.

19. The method of claim 14 wherein said nail means is chosen so as to have a transverse diameter that will produce an interference fit with the narrowest portion of said medullary canal.

20. The method of claim 14 further comprising the step of removing said nail means from said bone by coupling said insertion means to said nail means and throwing said throw weight against the other of said stop members so as to drive said nail means out of said bone.

21. A device for insertion into a bone, said bone having a medullary canal, a cortex and a fracture site, comprising:
  (a) an outer member having a longitudinal axis extending between first and second end portions, said outer member having an exterior surface and a transverse dimension which is small enough to allow the insertion of said outer member into the medullary canal of said bone, said outer member having a passage therein which passage extends between said first and second end portions, said passage having openings to communicate with said exterior surface said openings being located at said first and second end portions;
  (b) an inner member located in said passage, said inner member extending between said first and second end portions of said outer member, said inner member having first and second ends that are oriented so as to be adjacent to said first and second end portions of said outer member respectively, said inner member being movable longitudinally within said passage;
  (c) first holding means coupled to said inner member first end, said first holding means being adapted to engage said bone cortex, said first holding means being expandable into a deployed position from a stowed position, wherein said first holding means protrudes out from said outer member and through said outer member first end opening when said first holding means is in the deployed position and wherein when said first holding means is in the stowed position said first holding means is located in said outer member such that said outer member can be inserted into said medullary canal, said inner member moving longitudinally in said outer member to manipulate said first holding means between said deployed and stowed positions;
  (d) second holding means coupled to said inner member second end, said second holding means being adapted to engage said bone cortex;
  (e) retaining means for retaining said inner member in a position whereby said first holding means is in said deployed position, said retaining means being coupled to said inner and outer member;
  (f) means for adjusting the force exerted by said first and second holding means on said bone along said longitudinal axis, said force adjustment means being coupled with said first and second holding means, wherein said device is adapted to be inserted into the medullary canal of said bone so as to span the site of said bone fracture with said first holding means on one side of said fracture site and said second holding means on the other side of said fracture site, said device being adapted to exert compressive force onto said bone across said fracture site with said first and second holding means;
  (g) insertion means for inserting and removing said outer and inner members from said bone, said insertion means comprising a rod having a fixed end and a free end, said fixed end being adapted to be removably coupled to said inner member second end, said rod having stop members thereon, said rod having throw weight means thereon, said throw weight means being movable along said rod between said stop members.

22. A device for insertion into a bone, said bone having a medullary canal, a cortex and a fracture site, comprising:
  (a) an outer member having a longitudinal axis extending between first and second end portions, said outer member having an exterior surface and a transverse dimension which is small enough to allow the insertion of said outer member into the medullary canal of said bone, said outer member having a passage therein which passage extends between said first and second end portions, said passage having openings to communicate with said exterior surface, said openings being located at said first and second end portions;
  (b) an inner member located in said passage, said inner member extending between said first and second end portions of said outer member, said inner member having first and second ends that are oriented so as to be adjacent to said first and second end portions of said outer member respectively, said inner member being movable longitudinally within said passage;
  (c) first holding means coupled to said inner member first end, said first holding means being adapted to engage said bone cortex, said first holding means being expandable into a deployed position from a stowed position, wherein said first holding means protrudes out from said outer member and through said outer member first end opening when said first holding means is in the deployed position and wherein when said first holding means is in the stowed position said first holding means is located in said outer member such that said outer member can be inserted into said medullary canal, said inner member moving longitudinally in said outer member to manipulate said first holding means between said deployed and stowed positions;
  (d) second holding means coupled to said inner member second end, said second holding means being adapted to engage said bone cortex;
  (e) retaining means for retaining said inner member in a position whereby said first holding means is in said deployed position, said retaining means being coupled to said inner and outer member;
  (f) means for adjusting the force exerted by said first and second holding means on said bone along said longitudinal axis, said force adjustment means being coupled with said first and second holding means, wherein said device is adapted to be inserted into the medullary canal of said bone so as to span the site of said bone fracture with said first holding means on one side of said fracture site and said second means on the other side of said fracture site, said device being adapted to exert compressive force onto said bone across said fracture site with said first and second holding means;

(g) said retaining means comprising a retaining cap that is coupled to said outer member second end portion, said retaining cap having an opening that is aligned with said outer member second end portion opening, said retaining cap opening being of a smaller diameter than said inner member second end, wherein said cap opening limits the movement of said inner member towards said outer member second end portion when said arms are in said deployed position.

* * * * *